(12) United States Patent
Gebauer et al.

(10) Patent No.: US 8,754,111 B2
(45) Date of Patent: *Jun. 17, 2014

(54) METHOD AND SUBSTANCES FOR PREPARATION OF N-SUBSTITUTED PYRIDINIUM COMPOUNDS

(71) Applicant: Roche Diagnostics Operations, Inc., Indianapolis, IN (US)

(72) Inventors: Peter Gebauer, Penzberg (DE); Dieter Heindl, Paehl (DE); Carina Horn, Biblis (DE)

(73) Assignee: Roche Diagnostics Operations, Inc., Indianapolis, IN (US)

(*) Notice: Subject to any disclaimer, the term of this patent is extended or adjusted under 35 U.S.C. 154(b) by 0 days.

This patent is subject to a terminal disclaimer.

(21) Appl. No.: 13/945,556

(22) Filed: Jul. 18, 2013

(65) Prior Publication Data

US 2013/0303768 A1 Nov. 14, 2013

Related U.S. Application Data

(63) Continuation of application No. PCT/EP2012/050996, filed on Jan. 24, 2012.

(30) Foreign Application Priority Data

Jan. 26, 2011 (EP) .................................... 11152201

(51) Int. Cl.
| | | |
|---|---|---|
| C07D 213/08 | (2006.01) |
| C07D 213/14 | (2006.01) |
| C07D 211/70 | (2006.01) |
| C07D 211/82 | (2006.01) |
| C07D 213/46 | (2006.01) |
| A01N 43/40 | (2006.01) |
| A61K 31/44 | (2006.01) |
| C07C 291/00 | (2006.01) |
| C07C 257/00 | (2006.01) |
| C07C 263/00 | (2006.01) |
| C07C 265/00 | (2006.01) |

(52) U.S. Cl.
USPC ........... 514/355; 514/358; 514/352; 546/250; 546/347; 546/315; 564/279; 564/291

(58) Field of Classification Search
USPC .................. 546/250, 347; 514/355
See application file for complete search history.

(56) References Cited

U.S. PATENT DOCUMENTS 4,411,995 A 10/1983 Whitesides et al.
2003/0022266 A1* 1/2003 Fish et al. ....................... 435/25
(Continued)

FOREIGN PATENT DOCUMENTS

WO 2007/012494 A1 2/2007
WO 2010/094632 A1 8/2010
(Continued)

OTHER PUBLICATIONS

Dorwald; "Side Reactions in Organic Synthesis: A Guide to Successful Synthesis Design" 2005 Wiley-VCH Verlag GmbH & Co. KGaA, Wienheim, chapter 1.*

(Continued)

*Primary Examiner* — John Mabry
*Assistant Examiner* — Daniel Carcanague
(74) *Attorney, Agent, or Firm* — Armstrong Teasdale LLP

(57) ABSTRACT

A method for the synthesis of N-substituted 3-acylated pyridinium compounds by reacting a pentamethine precursor with a primary amine.

14 Claims, 1 Drawing Sheet

(56) References Cited

U.S. PATENT DOCUMENTS

2008/0213809 A1* 9/2008 Heindl et al. .................. 435/14
2012/0130062 A1* 5/2012 Duefel et al. ............. 536/26.24
2012/0190855 A1* 7/2012 Heindl et al. ................. 546/250

FOREIGN PATENT DOCUMENTS

WO 2011/012270 A1 2/2011
WO 2011/012271 A2 2/2011

OTHER PUBLICATIONS

International Search Report issued Mar. 12, 2012 in Application No. PCT/EP2012/050996, 4 pages.
Arnold, Z. and Holy, A., "The Preparation of Substituted Pentamethinium Salts," Collection of Czechoslovak Chemical Communications, 1965, pp. 40-46, vol. 30, No. 1.
Cheng, Wei-Chieh and Kurth, Mark J., "The Zincke Reaction, A Review," Organic Preparations and Procedures Int., 2002, pp. 585-608, vol. 34, No. 6.
Eda, Masahiro et al., "The Solid-Phase Zincke Reaction: Preparations of ω-Hydroxy Pyridinium Salts in the Search for CFTR Activation," Journal of Organic Chemistry, 2000, pp. 5131-5135, No. 65.
Genisson, Yves et al., "Zincke's Reaction with Chiral Primary Amines: A Practical Entry to Pyridinium Salts of Interest in Asymmetric Synthesis," Synlett, 1992, pp. 431-434, vol. 5.
Goulioukina, Natasha et al., "Synthesis of Nicotinamide Adenine Dinucleotide (NAD) Analogues with a Sugar Modified Nicotinamide Moiety," Helvetica Chimica Acta, 2007, pp. 1266-1278, vol. 90.
Kam, Bernard L. and Oppenheimer, Norman J., "Synthesis of a new class of D-aldopentofuranosylamines, the 5-O-trityl-D-aldopentofuranosylamines," Carbohydrate Research, 1979, pp. 275-280, vol. 77.
Kam, Bernard L. et al., "Pyridine Coenzyme Analogues. Synthesis and Characterization of α- and β-Nicotinamide Arabinoside Adenine Dinucleotides," Biochemistry, 1987, pp. 3453-3461, vol. 26.
Sicsic, Sames et al., "Activity of NMN+, nicotinamide ribose and analoges in alcohol oxidation promoted by horse-liver alcohol dehydrogenase, Improvement of this activity and structural requirements of the pyridine nucleotide part of the NAD+ coenzyme," European Journal of Biochemistry, 1986, pp. 403-407, vol. 155.
Vianna, Gustavo H. R. et al., "Rapid Microwave-Promoted Solvent-Free Synthesis of Zincke's Salts and their Conversion into Chiral Pyridinium Salts in Water," Letters in Organic Chemistry, 2008, pp. 396-398, vol. 5.
Wypych, Jean-Charles et al., "Reaction of Aldimine Anions with Vinamidinium Chloride: Three-Component Access to 3-Alkylpyridines and 3-Alkylpyridinium Salts and Access to 2-Alkyl Glutaconaldehyde Derivatives," Journal of Organic Chemistry, 2008, pp. 1169-1172, vol. 73.

* cited by examiner

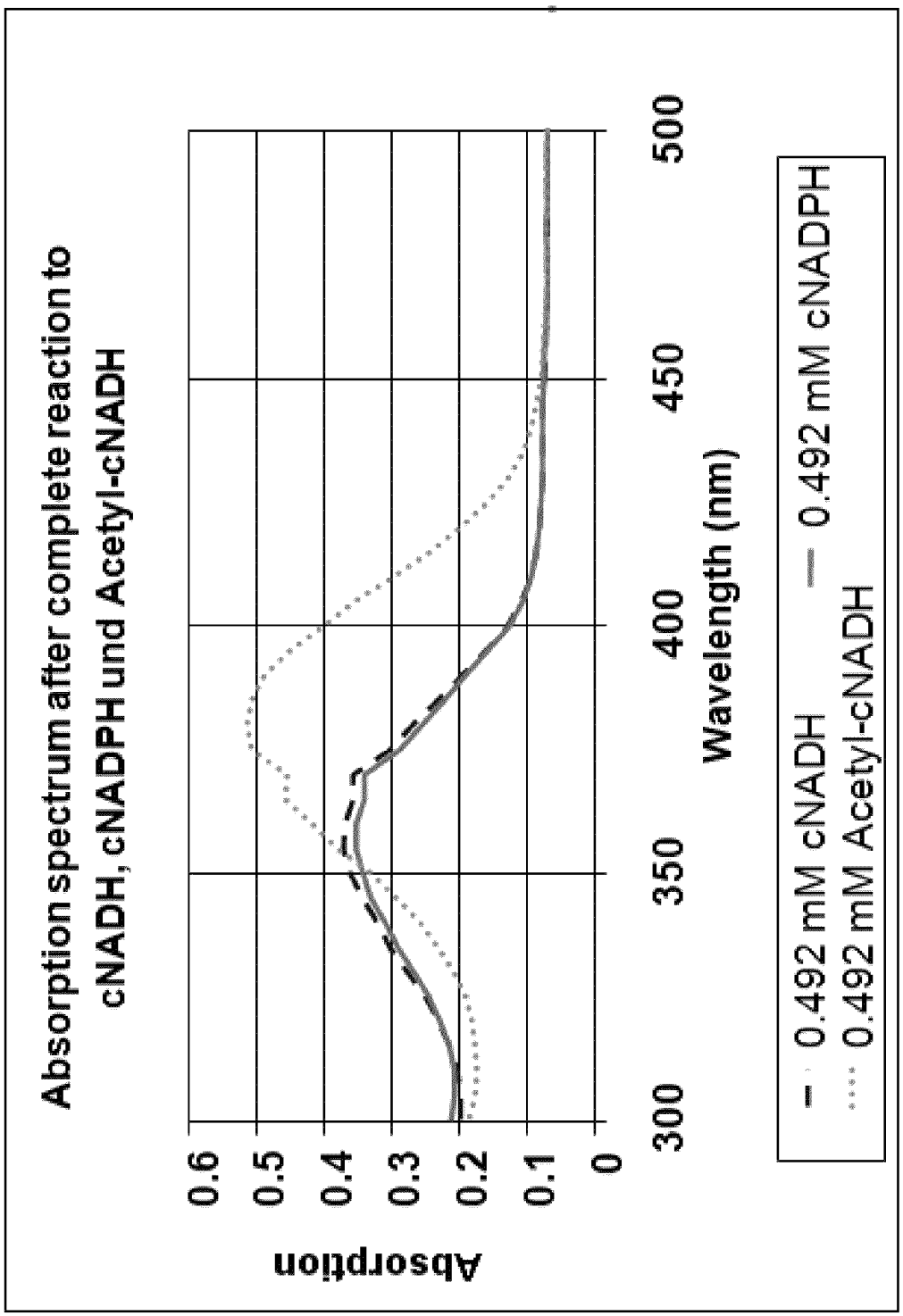

METHOD AND SUBSTANCES FOR PREPARATION OF N-SUBSTITUTED PYRIDINIUM COMPOUNDS

CROSS-REFERENCE TO RELATED APPLICATIONS

This application is a continuation of International Application No. PCT/EP2012/050996, filed Jan. 24, 2012, which claims the benefit of European Patent Application No. 11152201.7, filed Jan. 26, 2011, the disclosures of which are hereby incorporated by reference in their entirety.

BACKGROUND OF THE DISCLOSURE

Pyridinium compounds are of interest in drug design or as general intermediates for organic syntheses, e.g., especially in natural product synthesis. (Cheng, W.-C. and Kurth, M. J., Organic Preparations and Procedures International 34 (2002) 585-608). The standard synthetic route in the production of substituted pyridinium compounds is via alkylation of pyridine derivatives. However, this reaction is only convenient when using primary alkyl halides. When secondary or tertiary alkyl halides are used, elimination occurs as an unwanted side reaction and yields are generally low. Moreover when the alkylation is performed with alkyl halides with the halogen atom attached to an asymmetric carbon atom, racemization can occur during the nucleophilic displacement reaction.

These limitations may be overcome by using the "Zincke reaction" which is based on the reaction of Zincke salts with alkyl or aryl amines. Zincke salts are activated pyridinium salts which are capable of reacting with a primary amine (R—NH2), wherein at the nitrogen in 2 or 6 position, respectively, ring opening is induced which in turn is followed by ring closing to an R-substituted pyridinium compound. The Zincke reaction can also be performed with hydrazines, hydroxyl amines and carboxylic acid hydrazides. These types of Zincke reactions are used for in solution and for solid phase organic syntheses (Eda, M. et al., J. Org. Chem. 65 (2000) 5131-5135). In the art the predominant way for preparing the desired Zincke salts is by reacting a pyridine derivative with 2,4 dinitro halobenzol, for example, with 2,4 dinitrochlorbenzol and 2,4 dinitrobrombenzol.

As obvious from the above description of state of the art processes, the presently used activation reagents are either toxic, explosive, or otherwise hazardous and therefore limited to small scale research applications. There are scattered attempts to perform the Zincke reaction in an eco-friendly manner, e.g., by using microwave assisted synthesis. However this attempt still relies on explosive dinitrophenyl compounds and it is not possible to scale up this method without taking expensive precautionary measures (Vianna, G. H. R. et al., Letters in Organic Chemistry 5 (2008) 396-398). Another major limitation of the Zincke method is the fact that electron-poor reactants like 3-acyl substituted pyridines hardly react with 2,4-dinitro halogenated benzenes to the corresponding Zincke salts (Genisson, Y. et al., Synlett. 5 (1992) 431-434).

It is known that various 2-alkylaminopentadienimin derivatives react with NH4OAc or primary amines (R—NH2) under acidic conditions to the corresponding 3-alkylated pyridines, respectively, 1-R-3-alkyl-substituted pyridinium compounds. The required 2-alkylaminopentadienimin compounds are accessible from N-tertbutylimino derivatives of aldehydes, deprotonated with LDA and reacted with vinamidinium chloride (Wypych, J. C. et al., J. Org. Chem. 73 (2008) 1169-1172).

However, the utility of this method is unfortunately limited. No reactive groups, such as acyl functions, can be introduced in position 2 of the aminopentadienimin system, what, for example, would be a prerequisite for the synthesis of 1-R-3-acyl-substituted pyridinium compounds.

Therefore there is quite a need to improve the synthesis of N-substituted Acyl pyridinium compounds, for example by avoiding hazardous activation reagents. Novel less critical methods should allow for more safe production procedures and for easier, less risky and more efficient production of such compounds at much larger scale.

SUMMARY OF THE DISCLOSURE

The present disclosure relates to a method for the synthesis of N-substituted 3-acylated pyridinium compounds by reacting a pentamethine precursor with a primary amine. In this reaction an N-substituted 3-acyl pyridinium heterocycle is formed. As disclosed herein, the instant disclosure makes the surprising finding that quite some of the disadvantages of prior art procedures are overcome by use of the substances and methods as disclosed herein. For example, in an illustrative method according to the present disclosure first an aminopentadieniminium compound is provided. The subsequent reaction of this compound with a primary amine (R6-NH2) leads to the corresponding pyridinium compound that at position 1 is substituted with R6-. Methods disclosed herein, and discussed below, avoid the critical activation reagents as known in the art (and discussed above). Moreover, formation of the N-substituted pyridinium derivatives may be quantitative and can be scaled up easily.

According to some embodiments, the instant disclosure provides a method for the synthesis of an N-substituted 3-acyl pyridinium compound comprising the steps of a) providing an acyl pentamethinium salt b) reacting the pentamethinium salt of step (a) with a primary amine and c) thereby obtaining an N-substituted 3-acyl pyridinium compound. Embodiments disclosed herein are also useful in the synthesis of acyl-derivatives of NAD and NAD-analogs, like carba-NAD (=cNAD), respectively.

Also disclosed are novel acyl pentamethinium compounds.

BRIEF DESCRIPTION OF THE DRAWINGS

The features of this disclosure, and the manner of attaining them, will become more apparent and the disclosure itself will be better understood by reference to the following description of embodiments of the disclosure taken in conjunction with the accompanying drawing.

FIG. 1 illustrates the absorption spectra of cNADH (dashed line), cNADPH (continuous line) and Acetyl-cNADH (dotted line). The absorption maximum for Acetyl-cNADH is at about 380 nm and significant absorption is also shown at a wavelength of 400 nm or above.

Corresponding reference characters indicate corresponding parts throughout the several views. Although the drawings represent embodiments of the present disclosure, the drawings are not necessarily to scale and certain features may be exaggerated in order to better illustrate and explain the present disclosure. The exemplifications set out herein illustrate an exemplary embodiment of the disclosure, in one form, and such exemplifications are not to be construed as limiting the scope of the disclosure in any manner.

DETAILED DESCRIPTION OF THE EMBODIMENTS OF THE DISCLOSURE

The embodiments disclosed herein are not intended to be exhaustive or limit the disclosure to the precise form disclosed in the following detailed description. Rather, the embodiments are chosen and described so that others skilled in the art may utilize their teachings.

In a first embodiment the present disclosure relates to a method for synthesis of an N-substituted 3-alkylcarbonyl, 3-arylcarbonyl or 3-heteroarylcarbonyl pyridinium compound comprising the steps of a) providing an acyl pentamethinium salt b) reacting the pentamethinium salt of step (a) with a primary amine, and c) thereby obtaining an N-substituted 3-alkylcarbonyl, 3-arylcarbonyl or 3-heteroarylcarbonyl pyridinium compound. Substituted pyridinium compounds, according to the present disclosure, are of great utility in the synthesis of NAD and derivatives thereof as well in the synthesis of NAD analogs and derivatives thereof, respectively.

According to some embodiments the present disclosure provides a method for synthesis of an N-substituted 3-alkylcarbonyl, 3-arylcarbonyl or 3-heteroarylcarbonyl pyridinium compound comprising the steps of a) providing a pentamethinium salt according to Formula I,

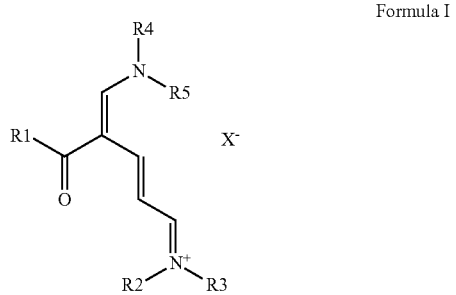

Formula I wherein X⁻ is a counter ion, R1 is selected from the group consisting of alkyl, aryl and heteroaryl, and R2 to R5 independently are methyl or ethyl;

b) reacting the pentamethinium salt of step (a) with a primary amine of Formula II,

Formula II wherein R6 is linear, branched, or cyclic, optionally substituted alkyl;

c) thereby obtaining an N-substituted pyridinium compound of Formula III,

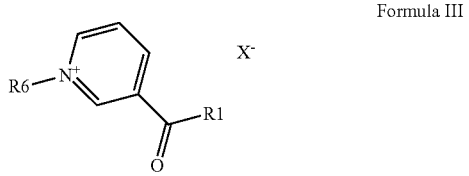

Formula III wherein X⁻, R1, and R6 are as defined above.

Exemplary counter ions (X⁻) include dodecyl sulfate, chloride, PF6⁻, BF4⁻, and ClO4⁻. In some illustrative embodiments the counter ion is dodecyl sulfate, tetrafluorophosphate or tetrafluoroborate.

In one embodiment the term alkyl comprises linear, branched and cyclic C1-C10 alkyl residues. In one embodiment the term aryl relates to aryl residues with 6 to 30 C atoms. Aryl e.g. is phenyl or naphthyl or higher condensed aromatic polycyclic with a total number of fused benzene rings up to 5. In one embodiment the heteroaryl group of the present disclosure has in total 6 to 30 atoms (6-30 atoms). Heteroaryl may comprise up to 5 heteroatoms, selected from S, O and N. Heteroaryl is for example furanyl, thiophenyl and pyridyl or imidazoyl which may be condensed to an aryl ring e.g., like in quinoline or benzofurane.

In one embodiment alkyl is C1-C10 alkyl, aryl is C6-C30 aryl and heteroaryl is a heteroaryl of 6 to 30 atoms (=6-30 atoms heteroaryl).

Any alkyl, aryl or heteroaryl can be substituted by any substituent which is inert under the given reaction conditions. For a skilled artisan it is standard to select such inert substituent.

The method according to the present disclosure is appropriate to produce alkylcarbonyl, arylcarbonyl as well as heteroarylcarbonyl pyridinium compounds.

In one embodiment the method according to the present disclosure is practiced with a pentamethinium compound according to Formula I, wherein R1 is methyl, ethyl, propyl, butyl or isopropyl. In one embodiment the present disclosure relates to the use of a pentamethinium salt in a method according to the present disclosure, wherein R1 is CH3, i.e. to the production of a N-substituted 3-acetyl pyridinium compound.

In one embodiment the method according to the present disclosure is practiced with a pentamethinium compound according to Formula I, wherein R2 to R5 are methyl.

In some embodiments the present disclosure relates to a method for synthesis of an N-substituted 3-alkylcarbonyl pyridinium compound comprising the steps of (a) providing a pentamethinium salt according to Formula I,

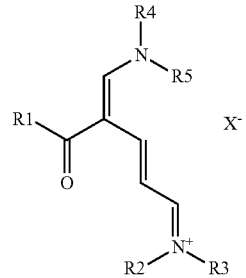

Formula I wherein X⁻ is a counter ion, R1 is C1-C10 alkyl R2 to R5 independently are methyl or ethyl, b) reacting the pentamethinium salt of step (a) with a primary amine of Formula II,

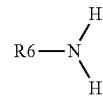

Formula II wherein R6 is linear, branched, or cyclic, optionally substituted alkyl, c) thereby obtaining an N-substituted pyridinium compound of Formula III,

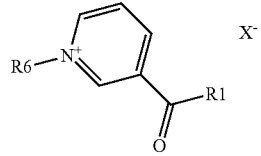

Formula III wherein X⁻, R1 and R6 are as defined above.

As defined above, R6 is linear or branched, or cyclic, optionally substituted alkyl. In an illustrative embodiment alkyl is a linear C1-C6 alkyl, or a branched C3-C6 alkyl, or a cyclic C5-C6 alkyl, or substituted alkyl is a substituted linear C1-C6, or a substituted branched C3-C6, or a substituted cyclic C5-C6 alkyl. In some embodiments the compound according to Formula II is a linear or branched alkyl amine or is a furanosylamine or a cyclopentylamine. In one embodiment R6 is a furanosyl or a cyclopentyl residue.

It has surprisingly been found that the synthesis according to the present disclosure has very high yields of the desired product. Thus, despite the basic conditions no significant side reactions with the CH acid acyl function could be observed.

The method according to the present disclosures is especially useful in the synthesis of acyl pyridinium derivatives, for example. We, for example, found that the pentamethinium salt 5-dimethylamino-4-acetyl-penta-2,4-dienylidene-dimethylammonium tetrafluoroborate cyclizises with different primary amines (R—NH2) in one step to the corresponding 1-R-3-acyl-substituted pyridinium compound. Using this method, it is possible to obtain 3-Acetyl-1-[2,3-bishydroxy-4-(phosphonooxy)methyl-cyclopentyl]-pyridinium as diisopropylethyl-ammonium salt, for example. This compound is an excellent precursor in the synthesis of the 3-acetyl derivative of carbaNAD (=cNAD).

In one embodiment the method according to the present disclosure is practiced with the primary amine according to Formula II being 3-Amino-5-(phosphonooxymethyl)-1,2-cyclo-pentanediol. This compound according to Formula II is also known as 2,3-Dihydroxy-4-phosphono-oxymethyl-1-aminocyclopentane or as Phosphoric acid mono-(4-amino-2,3-dihydroxy-cyclopentylmethyl)ester. As the skilled artisan will appreciate this compound and the relating compounds are conveniently provided as diammonium salts.

In one embodiment the method according to the present disclosure is practiced with the primary amine according to Formula II being (1R,2S,3R,4R)-2,3-Dihydroxy-4-phosphono-oxymethyl-1-aminocyclopentane.

In one embodiment the method according to the present disclosure is practiced with the primary amine according to Formula II being (1R,2S,3R,4R)-2,3-Dihydroxy-4-hydroxymethyl-1-aminocyclopentane.

Surprisingly it has been found that it is possible to produce and to provide, for example, by the method disclosed in the Examples section, novel pentamethinium compounds to the public. In one embodiment the present disclosure relates to a compound of Formula I,

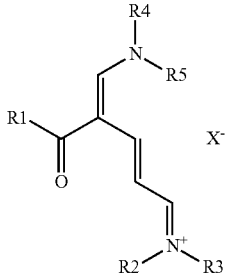

Formula I wherein X⁻ is a counter ion, R1 is selected from the group consisting of C1-C10 alkyl, C6-C30 aryl and heteroaryl with 6-30 atoms and R2 to R5 independently are methyl or ethyl.

In one embodiment the present disclosure relates to a pentamethinium compound according to Formula I, wherein R1 is C1-C10 alkyl. In some embodiments the present disclosure relates to a pentamethinium compound according to Formula I, wherein R1 is selected from the group consisting of methyl, ethyl, propyl, butyl and isopropyl. In some embodiments the present disclosure relates to a pentamethinium compound according to Formula I, wherein R1 is methyl.

The experiments disclosed in the Examples section demonstrates a conversion of the pentamethinium salt 5-dimethylamino-4-acetyl-penta-2,4-dienylidene-dimethylammonium tetrafluoroborate with 3-Amino-5-[(phosphonooxy)methyl]-1,2-cyclo-pentanediol diammonium salt. It has been found that the phosphorylated aminosugar reacts almost quantitatively with the pentamethinium salt, e.g. in the presence of tetrafluoroborate as a counter ion, to obtain the N-substituted 3-acetyl pyridinium derivative.

The presented method can, however, be extended to other primary amines. As the skilled artisan appreciates such primary amines can comprise further substituents which do not interfere with the cyclization reaction. In an illustrative embodiment the compound R6-NH2 is a substituted primary alkyl amine.

Exemplary substituted primary alkyl amines for use in a method according to the present disclosure are pure stereoisomers of amino alcohols and amino acids.

Exemplary amino alcohol may be derived from any naturally occurring or any commercially available non-natural amino acid. For example the amino alcohol may be selected from the group consisting of serinol, threoninol, phenylalaninol, 2,5-diamino-1-pentanol (from ornithine), 2,6-diamino-1-hexanol (from lysine).

In embodiments in which the compound according to Formula II is an amino acid, the amino acid may be selected from any naturally occurring or any non-natural amino acid. In an illustrative embodiment the amino acid either is a naturally occurring amino acid or a non-naturally occurring, in some cases even commercially available, amino acid. In some embodiments the compound according to Formula II is an amino acid selected from serine threonine, phenylalanine, ornithine, lysine, and leucine.

A further alternative embodiment di- or polyamines where no amino group is protected can be reacted with two or more equivalents of the pentamethinium salt, in order to form di-pyridinium or poly-pyridinium compounds.

Also exemplary primary amines include amines substituted with furanosyl sugar moieties or analogs of such furanosyl sugar moieties, which optionally are phosphorylated at an OH group or compromise protected hydroxyl groups, whereas the protecting groups are benzyl, acetal, silyl and trityl or compromise F or methoxy groups instead of OH groups. For example a furanosyl sugar or such analogs which are suitable for the synthesis of NAD or Nicotinamidmononucleosid and analogs thereof are used.

The use of furanosylamines for the synthesis of NAD or Nicotinamidmononucleosid and analogs thereto is described in detail in the following references: Kam, B. L. et al., Biochemistry 26 (1987) 3453-3461; Sicsic, S. et al., European Journal of Biochemistry 155 (1986) 403-407; Kam, B. L. and Oppenheimer, N. J., Carbohydrate Research 77 (1979) 275-280; and U.S. Pat. No. 4,411,995. Exemplary furanosylamines according to the instant disclosure include the beta and alpha amino anomers of D- and L-ribose, xylose and arabinose. Exemplary cyclopentylamines include the carba analogues of furanosylamines like Beta-D-ribofuranosyl amines, 2-deoxyribofuranosylamine, or 2,3-dideoxy-ribosyl-furanosylamine i. e. (1R,2S,3R,4R)-2,3-Dihydroxy-4-hydroxymethyl-1-aminocyclopentane, (1S,3R,4R)-3-Amino-4-hydroxy-cyclo-pentanemethanol, or (1R-cis)-3-amino-cyclopentane-methanol.

The method disclosed in the present disclosure in one embodiment is used in the synthesis of the NAD-analog carba-NAD (=cNAD) and of derivatives thereof, respectively.

It is especially useful in the synthesis of the acylated derivatives of cNAD. Carba-NAD and uses are described in detail in WO 2007/012494. The full disclosure of WO 2007/012494 is herewith included by reference. Exemplary embodiments include a method in which a pentamethinium salt is reacted with a primary amine, wherein said primary amine is (1R,2S, 3R,5R)-3-Amino-5-[(phosphonooxy)methyl]-1,2-cyclopentanediol diammonium salt. Reacting 5-Dimethylamino-4-acetyl-penta-2,4-dienylidene-dimethylammonium tetrafluoroborate with this primary amine leads to the formation of (1R,2S,3R,4R) 3-Acetyl-1-[2,3-bishydroxy-4-(phosphono-oxy)methyl-cyclopentyl]-pyridinium (diisopropylethylammonium salt) which is the key to the synthesis of the acetyl analog to cNAD (Acetyl-cNAD refers to a compound where the carboxamido group is substituted by an acetyl group). Carba-NAD and analogues and exemplary uses are described in detail in WO 2007/012494. The full disclosure of WO 2007/012494 is herewith included by reference.

Other exemplary substituted primary amines are selected from 3-Amino tetrahydrofuranes or protected 3-Amino-pyrollidines, e. g. (2R,4R)-4-Aminotetrahydrofuran-2-methanol (a heterocyclic analog of 2,3-dideoxyribosylamine) cyclohexylamines and cyclohex-2-enyl amines, e.g. 6 ring sugar analogs as disclosed by Goulioukina, N. et al., Helvetica Chimica Acta 90 (2007) 1266-1278.

Exemplary examples of phosphorylated amino sugars are (1R,4S,6S)-4-Amino-6-hydroxy-2-cyclohexene-1-methanol-1-(dihydrogen phosphate), 2-Amino-1,5-anhydro-2-deoxy-6-(dihydrogen phosphate) D-altritol, 2-Amino-1,5-anhydro-2,3-dideoxy- and 6-(dihydrogen phosphate) D-arabino-hexitol.

As the skilled artisan will appreciate even primary amines having an additional principally nucleophilic substituent can be used. In this case the further nucleophilic group has to be protected by an appropriate protecting group. Protecting groups are well known from the art and reviewed in standard text books (Greene, T. W., Protective groups in organic synthesis, John Wiley&Sons, Inc. (1981) New York, Chichester, Brisbane, Toronto). In some embodiments, amino groups are protected by boc-, phthaloyl- or trifluoracetyl-protecting groups, mercapto groups are protected as disulfide.

Also it has surprisingly been found by the inventors that the emission wavelength is shifted to longer wavelengths (400 nm) as compared to non acylated NAD and/or cNAD forms. This is a significant advantage in order to avoid the interference from auto-flourescent compounds comprised in (biological) samples.

The following examples, sequence listing, and figures are provided for the purpose of demonstrating various embodiments of the instant disclosure and aiding in an understanding of the present disclosure, the true scope of which is set forth in the appended claims. These examples are not intended to, and should not be understood as, limiting the scope or spirit of the instant disclosure in any way. It should also be understood that modifications can be made in the procedures set forth without departing from the spirit of the disclosure.

Illustrative Embodiments

The following comprises a list of illustrative embodiments according to the instant disclosure which represent various embodiments of the instant disclosure. These illustrative embodiments are not intended to be exhaustive or limit the disclosure to the precise forms disclosed, but rather, these illustrative embodiments are provided to aide in further describing the instant disclosure so that others skilled in the art may utilize their teachings.

1. A method for synthesis of an N-substituted 3-alkylcarbonyl, 3-arylcarbonyl or 3-heteroarylcarbonyl pyridinium compound comprising the steps of
  a) providing a pentamethinium salt according to Formula I,

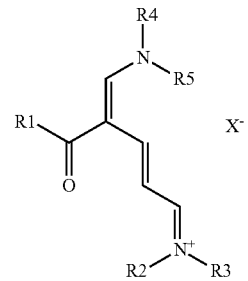

Formula I wherein, X⁻ is a counter ion, R1 is selected from the group consisting of alkyl, aryl and heteroaryl, and R2 to R5 independently are methyl or ethyl,
  b) reacting the pentamethinium salt of step (a) with a primary amine of Formula II,

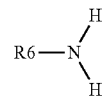

Formula II wherein R6 is linear, branched, or cyclic, optionally substituted alkyl,
  c) thereby obtaining an N-substituted pyridinium compound of Formula III,

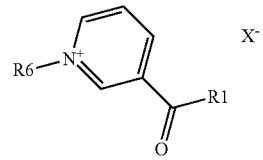

Formula III wherein X⁻, R1, and R6 are as defined above.
2. The method according to embodiment 1, wherein R1 is methyl, ethyl, propyl, butyl or isopropyl.
3. The method according to embodiments 1 or 2, wherein R2 to R5 are methyl.
4. The method according to any of embodiments 1 to 3, wherein the primary amine according to Formula II is 3-Amino-5-[(phosphonooxy)methyl]-1,2-cyclo-pentanediol.
5. The method according to any of claims 1 to 4, wherein the primary amine according to Formula II is (1R,2S,3R,5R)-3-Amino-5-[(phosphono-oxy)methyl]-1,2-cyclo-pentanediol.
6. The method according to any of claims 1 to 5, wherein the primary amine according to Formula II is (1R,2S,3R,4R)-2,3-Dihydroxy-4-hydroxymethyl-1-aminocyclopentane.

7. A compound of Formula I,

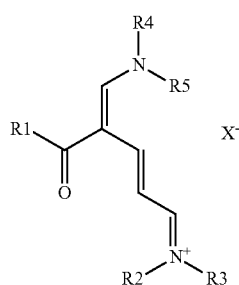

Formula I wherein, X⁻ is a counter ion, R1 is selected from the group consisting of C1-C10 alkyl, C6-C30 aryl and heteroaryl with 6 to 30 atoms, and R2 to R5 independently are methyl or ethyl.

8. The compound according to claim 7, wherein R1 is C1-C10 alkyl.
9. The compound according to claim 7 or 8, wherein R1 is selected from the group consisting of methyl, ethyl, propyl, butyl and isopropyl.
10. The compound according to claim 9, wherein R1 is methyl.

EXAMPLES

Example 1

Synthesis of ((1R,2S,3R,4R)-2,3-Dihydroxy-4-hydroxymethyl-cyclopentyl)-carbamic acid 9H-fluoren-9-ylmethyl ester

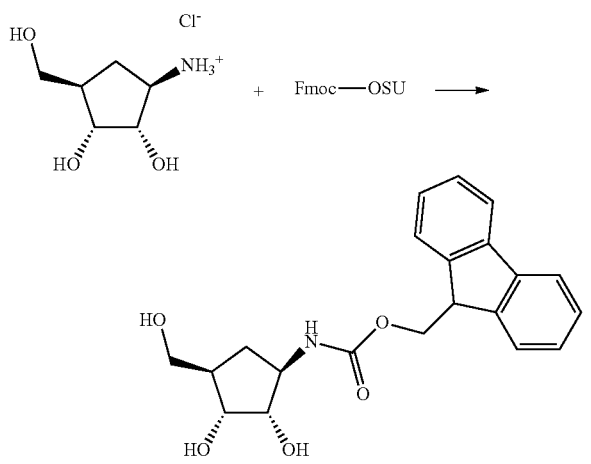

(1R,2S,3R,4R)-2,3-Dihydroxy-4-(hydroxylmethyl)-1-aminocyclopentan hydro-chloride (70.0 g, 380 mmol) was dissolved in water (660 ml) and FmocOSU (N-(9-Fluorenyl-methoxycarbonyloxy)-succinimid) (148.5 g, 440 mmol) solved in dioxan (2.00 l) was added. Then saturated sodium hydrogencarbonate solution (800 ml, 880 mmol) was added slowly. The mixture was stirred 3 h at room temperature until TLC (Silicagel Merck 60, chloroform/methanol/acetic acid 8:2+0.1% v/v/v) showed complete consumption of the educts. The obtained precipitate was filtered off and the filtrate was added to water (6.00 l). The resulting suspension was stirred for 5 min and then stored 12 h at 4° C. The resulting suspension was filtered. The obtained solid was washed with cold water (3.00 l) and dried 12 h under reduced pressure at 45° C. over calcium chloride. For a further purification the crude product was suspended in ethylacetate, stirred 1 h, filtered and dried under reduced pressure yielding 134 g (95%) of the title compound as white solid.

Example 1.2

Synthesis of ((3aS,4R,6R,6aR)-6-Hydroxymethyl-2,2-dimethyl-tetrahydro-cyclopenta[1,3]dioxol-4-yl)-carbamic acid 9H-fluoren-9-ylmethyl ester

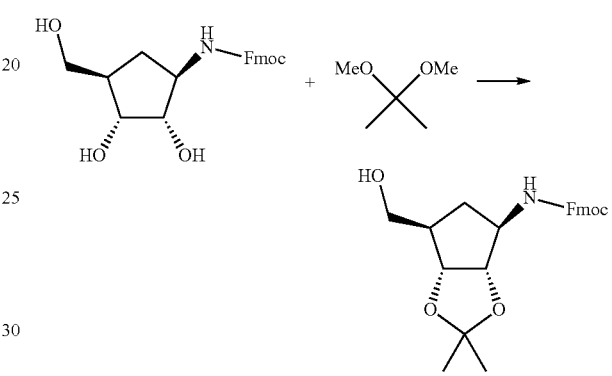

((1R,2S,3R,4R)-2,3-Dihydroxy-4-hydroxymethyl-cyclopentyl)-carbamic acid 9H-fluoren-9-ylmethyl ester (115 g, 310 mmol), 2,2-dimethoxypropane (360 ml, 3.10 mol) and p-toluenesulfonic acid monohydrate (118 g, 620 mmol) were dissolved in dry acetone (2.00 l). The mixture was stirred for 3.5 h at room temperature to the complete consumption of the starting material according to TLC (Silicagel Merck 60, chloroform/methanol/acetic acid 9:1+0.1% v/v/v). The resulting suspension was stirred 15 min at 0° C. and the precipitate was filtered off and washed with cold acetone. The obtained brown solid was suspended again in diethylether (800 ml) and stirred for 20 min, filtered off, washed with diethylether (400 ml) and dried 8 h under reduced pressure giving 116 g (91%) of the title compound.

Example 1.3

Synthesis of ((1R,2S,3R,4R)-2,3-Dihydroxy-4-phosphono-oxymethyl-cyclopentyl)-carbamic acid 9H-fluoren-9-ylmethyl ester

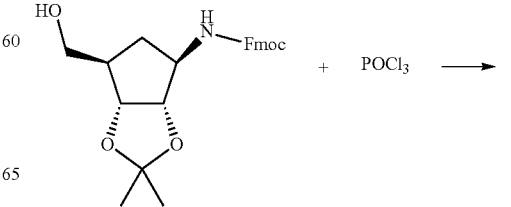

Example 1.4

Synthesis of (1R,2S,3R,5R)-3-Amino-5-[(phosphono-oxy)methyl]-1,2-cyclo-pentanediol diammonium salt

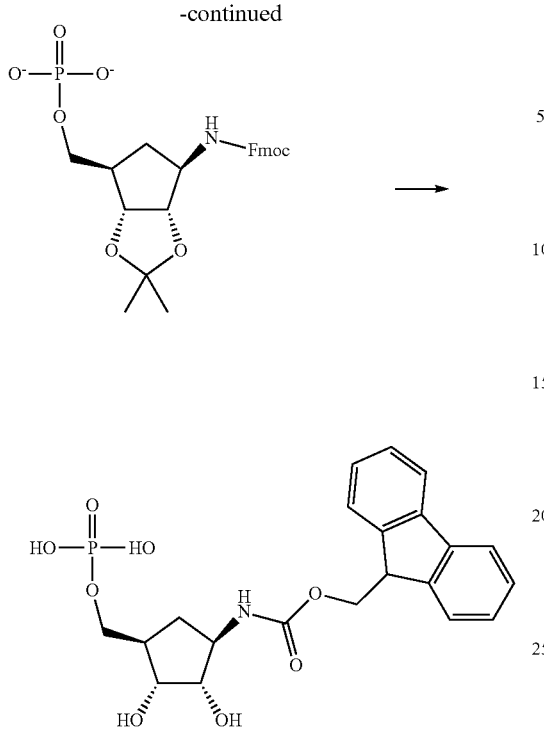

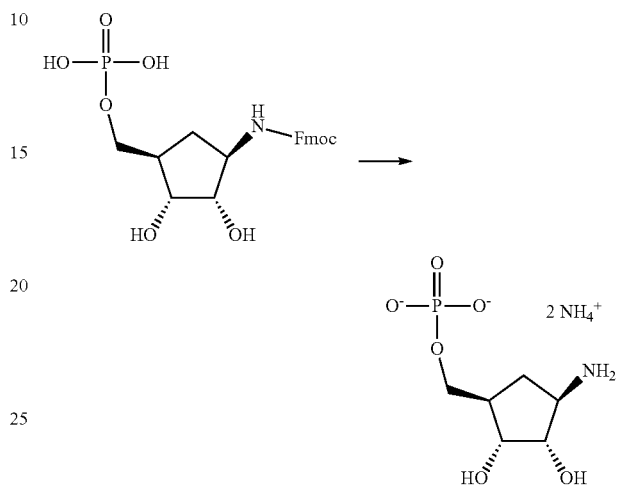

A three-necked flask fitted with thermometer was filled with ((3aS,4R,6R,6aR)-6-Hydroxymethyl-2,2-dimethyl-tetrahydro-cyclopenta[1,3]dioxol-4-yl)-carbamic acid 9H-fluoren-9-ylmethyl ester (146 g, 357 mmol) followed by dry trimethylphosphate (1.80 l) dissolving almost the complete solid. Under cooling with an ice bath freshly distilled phosphoroxychloride (305 ml, 3.33 mol) dissolved in dry trimethylphosphate (200 ml) was added dropwise over a period of 1 h taking care the temperature of the mixture did not rise above 10° C. Under the same conditions dry pyridine (80.0 ml, 991 mmol) was added and the mixture was stirred 2 h under ice cooling. After the mixture was left 1 h at room temperature it was dropped slowly over a period of 3 h into a saturated solution of sodium hydrogencarbonate (7.00 l). If the reaction mixture is getting to hot it is cooled with an ice bath. After complete addition the mixture is still acidic (pH=2). The resulting suspension is stored 12 h at 4° C. The obtained precipitate was filtered off and the filtrate was stirred with a saturated solution of sodium chloride (30.0 l). Following the mixture was left 12 h at 4° C. and the resulting precipitate was filtered off or centrifuged. The residue was added to water (13.0 l) and stirred vigorously for 2 h. Under slower stirring wet diaion (Supelco HP-20) (5.00 l) was added and the mixture was further stirred for 45 min. Following the diaion was decanted and washed two times with water (5.00 l) in the same way. The loaded diaion was filled in a chromatography column and eluted with 25% isopropanol yielding 76.0 g (46%) of the title compound.

((1R,2S,3R,4R)-2,3-Dihydroxy-4-phosphono-oxymethyl-cyclopentyl)-carbamic acid 9H-fluoren-9-ylmethyl ester (42.4 g, 94.3 mmol) was suspended in methanol (200 ml) followed by the addition of an ammonia solution (25% in $H_2O$, 500 ml). The mixture was stirred for 12 h at room temperature. The resulting precipitate was filtered off and the filtrate was evaporated under reduced pressure. The residue was dissolved in water (500 ml) and lyophilized yielding 24.4 g (99%) of the title compound.

Example 2

Synthesis of Pyridinium Tetrafluoroborate

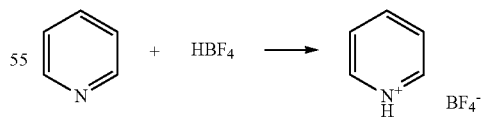

Tetrafluoroboric acid (250 ml, 2.00 mol) was added to cool (0° C.) pyridine (157.7 ml, 1.95 mol) within 25 min obtaining a colorless precipitate. After the acid was completely added the mixture was further stirred for 30 min at the same temperature. Then the reaction mixture was filtered. The residue was washed twice with cold ethanol and dried 12 h at high vacuum to yield 201.9 g (60%) pyridinium tetrafluoroborate as colorless crystals.

Example 3

Synthesis of 5-Dimethylamino-4-acetyl-penta-2,4-dienylidene-dimethylammonium tetrafluoroborate

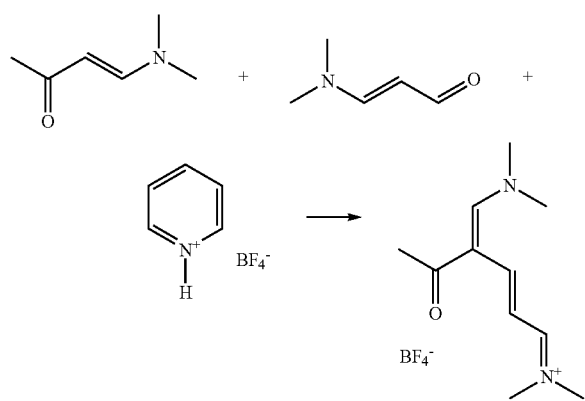

Pyridinium tetrafluoroborate (2.21 g, 13.3 mmol) was added to a solution of (3E)-4-(dimethylamino)-3-buten-2-one (1.54 ml, 13.3 mmol) in 13.5 ml acetic anhydride/acetic acid (2:1). The resulting suspension was cooled to 0° C. and 3-dimethylaminoacroleine (1.33 ml, 13.3 mmol) was added over a period of 1 h under vigorous stirring and cooling with an ice bath receiving a red-brown precipitate. The cool reaction mixture was filtered and the remaining solid was washed with diethylether several times and dried under reduced pressure. The pentamethinium salt was obtained as orange crude product (2.69 g, 96%) and was used without any further purification.

Example 4

Synthesis of 3-Acetyl-1-[(1R,2S,3R,4R)-2,3-bishydroxy-4-(phosphonooxy)methyl-cyclopentyl]-pyridinium diisopropylethylammonium salt

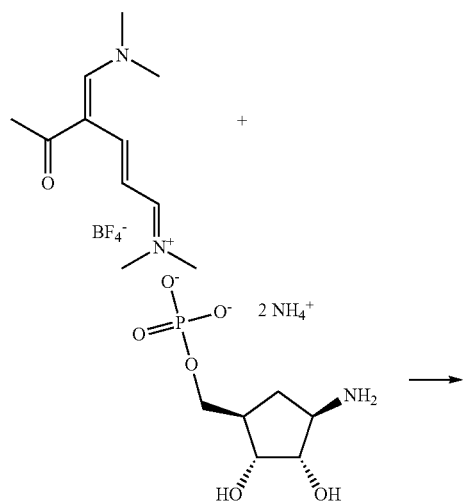

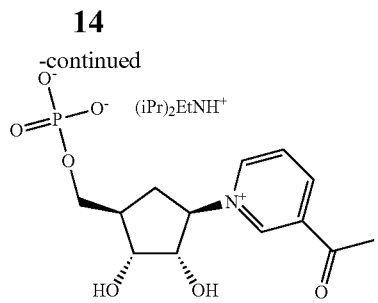

(1R,2S,3R,5R)-3-Amino-5-[(phosphonooxy)methyl]-1,2-cyclo-pentanediol diammonium salt (3.22 g, 12.3 mmol) was dissolved in 20.0 ml methanol/$H_2O$ (1:1). Then diisopropylethylamine (4.00 ml, 23.0 mmol) was added followed by evaporating under reduced pressure. This procedure was repeated two times. The obtained, dried solid was suspended in 100.0 ml MeOH and 5-Dimethylamino-4-acetyl-penta-2,4-dienylidene-dimethylammonium tetrafluoroborate (2.49 g, 8.83 mmol, crude product from example 3) was added. The suspension was mixed with diisopropylethylamin (3.06 ml, 17.6 mmol) and refluxed for 45 min. After cooling down to room temperature 300 ml ethylacetate was added. The resulting precipitate was filtered off and dried briefly under reduced pressure. The obtained solid was dissolved in water, purified with activated charcoal (5.00 g), filtered and lyophilized yielding 3.47 g of a strong hygroscopic red-brown solid (corresponding 85% of the pyridinium salt). This prepurified material mainly contains the title compound (according HPLC/MS) and was used for further reactions in the present purity.

Example 5

Synthesis of Acetyl-cNAD (Enzymatic)

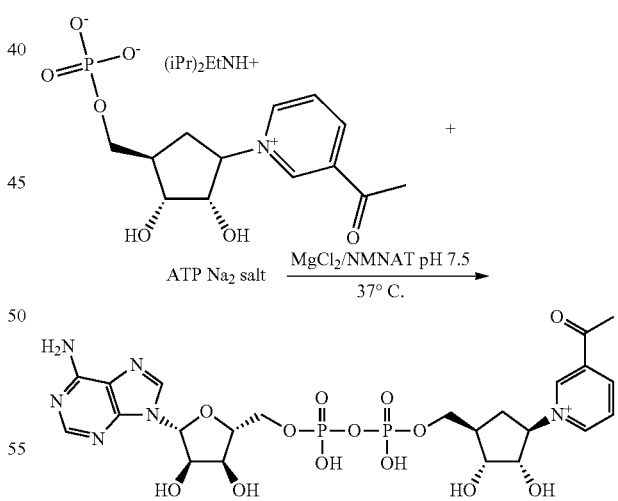

3-Acetyl-1-[(1R,2S,3R,4R)-2,3-bishydroxy-4-(phosphonooxy)methyl-cyclo-pentyl]-pyridinium diisopropylethylammonium salt (3.55 g, 7.71 mmol), ATP disodium salt (6.99 g, 11.6 mmol) and magnesium chloride hexahydrate (568 mg, 2.79 mmol) were dissolved in 180 ml water. After setting the pH to 7.5 with 10M NaOH an enzyme suspension of nicotinamide mononucleotide adenylyltransferase NMNAT3 (human, recombinant) (EC 2.7.7.1) from Axxora ALX-201-238 (3.00 ml, 162 U/g) was added. The mixture was stirred at 37°

C. After 16 h again 1.00 ml enzyme suspension was added. This procedure was repeated after another 8 h. After further 16 h stirring at 37° C. nearly almost of the phosphorylated aminosugar has been reacted to the title compound (according to HPLC/MS).

Example 6

Enzymatic Reduction of Acetyl-cNAD, cNAD, cNADP

Acetyl-cNADH and for comparison cNAD, cNADP were reduced by using GlucDH mut 2 (WO2010/094632) using the following conditions:
Chemicals:

| |
|---|
| NaCl (Merck.1.02406.0080) |
| Tris (708 976 von Roche) |
| D(+)-Glucose monohydrate p.a. (Merck 8342) |
| Acetyl-cNAD (free acid) |
| Bidest. Water (Millipore) |
| HCl 1N (Merck 1.09973.0001) |

A Dilution Buffer (NaCl 0.2 Mol/l; Tris 0.1 Mol/l; pH 8.5) was Prepared as Follows:

11.7 g NaCl and 12.1 g Tris (=tris(hydroxyethyl)amin) were dissolved in 900 ml bidest. water and the pH was adjusted to pH 8.5 by addition of HCL 1N and filled to 1.00 l with bidest. Water.

Glucose-Solution:

2.00 g D(+)-Glucose-Monohydrate were dissolved in 10.0 ml bidest. water. The solution is ready for usage after 2 h at room temperature.

GlucDH2-Stock-Solution:

10.0 mg of the enzyme (Lyo) were dissolved in 1.00 ml Tris-buffer.

Reduction of Acetyl-cNAD-Solution (15 mmol/l):

9.90 mg Acetyl-cNAD (Mw=659.47 g/mol) were dissolved in 1.00 ml bidest. water.

100 µl GlucDH2-stock-solution were dissolved in 0.90 ml dilution buffer (dilution factor=10).

Reduction of cNADP (15 mmol/l):

10 µl GlucDH2-stock-solution were dissolved in 0.99 ml dilution-buffer. 100 µl of this solution were dissolved in 0.40 ml dilution buffer (dilution factor=500).

Reduction of cNAD (15 mmol/l):

10 µl GlucDH2-stock-solution were dissolved in 0.99 ml dilution buffer. 100 µl of this solution were dissolved in 0.30 ml dilution buffer (dilution factor=400).

1. The tempered (25° C.) reagent solutions were pipetted into a 1 cm plastic cuvette as follows:

| | |
|---|---|
| Tris-buffer | 2.70 ml |
| Glucose solution | 0.20 ml |
| Acetyl-cNAD - solution or cNAD or cNADP (15 mmol/l) | 0.10 ml |

After mixing and tempering to 25° C., the reaction was started by addition of 0.05 ml the above mentioned corresponding GlucDH2-solutions. An UV/VIS spectra was recorded after 30 min.

From this experiment it is obvious that Acetyl-cNAD also serves as a coenzyme for a dehydrogenase.

Also it has been found that the absorption wavelength is shifted to longer wavelengths (maximum close to 400 nm) as compared to non acylated NAD and/or cNAD forms. Corresponding absorption spectra are shown in FIG. 1. This is a significant advantage for redox-based assays, since it allows to reduce or avoid the interference from auto-fluorescent compounds comprised in (biological) samples All references cited in this specification are herewith incorporated by reference with respect to their entire disclosure content and the disclosure content specifically mentioned in this specification.

While this disclosure has been described as having an exemplary design, the present disclosure may be further modified within the spirit and scope of this disclosure. This application is therefore intended to cover any variations, uses, or adaptations of the disclosure using its general principles. Further, this application is intended to cover such departures from the present disclosure as come within the known or customary practice in the art to which this disclosure pertains.

What is claimed is:

1. A method of synthesizing a N-substituted 3-alkylcarbony pyridinium compound of Formula III,

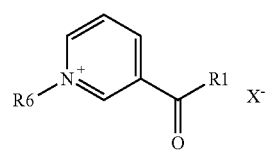

Formula III the method comprising the steps of:
a) providing a pentamethinium salt according to Formula I,

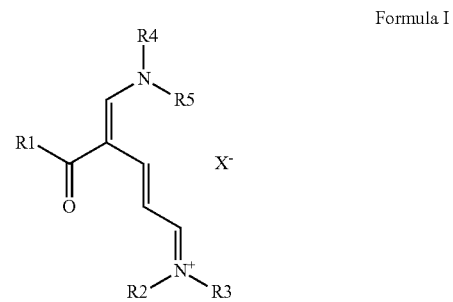

Formula I wherein, X⁻ is a counter ion, R1 is alkyl, and R2, R3, R4 and R5, independently, are methyl or ethyl,
b) reacting the pentamethinium salt of step (a) with a primary amine of Formula II,

Formula II wherein R6 is substituted linear, branched, or cyclic alkyl or unsubstituted linear, branched, or cyclic alkyl.

2. The method according to claim 1, wherein R1 is methyl, ethyl, propyl, butyl or isopropyl.

3. The method according to claim 1, wherein R2, R3, R4 and R5 are methyl.

4. The method according to claim 1, wherein the primary amine of Formula II is 3-Amino-5-[(phosphonooxy)methyl]-1,2-cyclo-pentanediol.

5. The method according to claim 1, wherein the primary amine of Formula II is (1R,2S,3R,5R)-3-Amino-5-[(phosphono-oxy)methyl]-1,2-cyclo-pentanediol.

6. The method according to claim 1, wherein the primary amine of Formula II is (1R,2S,3R,4R)-2,3-Dihydroxy-4-hydroxymethyl-1-aminocyclopentane.

7. The method according to claim 1, wherein R6 is linear $C_1$-$C_6$ alkyl.

8. The method according to claim 1, wherein R6 is substituted branched C3-C6 alkyl.

9. The method according to claim 1, wherein R6 is substituted cyclic C5-C6 alkyl.

10. The method according to claim 1, wherein R6 is a substituted or unsubstituted cyclopentyl residue.

11. A compound of Formula I,

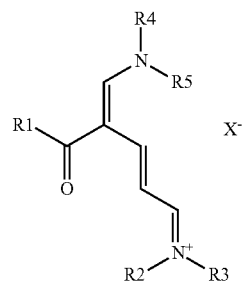

Formula I wherein, $X^-$ is a counter ion, R1 is alkyl, and R2, R3, R4 and R5, independently, are methyl or ethyl.

12. The compound according to claim 11, wherein R1 is C1-$C_{10}$ alkyl.

13. The compound according to claim 11, wherein R1 is selected from the group consisting of methyl, ethyl, propyl, butyl and isopropyl.

14. The compound according to claim 13, wherein R1 is methyl.

* * * * *